United States Patent [19]

Edelson

[11] Patent Number: 4,612,007

[45] Date of Patent: * Sep. 16, 1986

[54] METHOD AND SYSTEM FOR EXTERNALLY TREATING THE BLOOD

[76] Inventor: Richard L. Edelson, 3 Rall Ct., Roseland, N.J. 07068

[*] Notice: The portion of the term of this patent subsequent to Aug. 16, 2000 has been disclaimed.

[21] Appl. No.: 447,891

[22] Filed: Dec. 8, 1982

Related U.S. Application Data

[63] Continuation-in-part of Ser. No. 274,319, Jun. 16, 1981, and Ser. No. 272,981, Jun. 12, 1981, which is a continuation-in-part of Ser. No. 102,553, Dec. 11, 1979, Pat. No. 4,321,919.

[51] Int. Cl.$^4$ ............................................. A61M 1/03
[52] U.S. Cl. ........................................ 604/5; 128/1 R; 128/395; 128/DIG. 3; 604/20; 604/28; 422/44
[58] Field of Search ................. 604/4, 6, 5, 20, 28; 128/1 R, 395, DIG. 3; 422/44

[56] References Cited

U.S. PATENT DOCUMENTS

| | | | |
|---|---|---|---|
| 1,683,877 | 9/1928 | Edblom et al. | |
| 3,325,641 | 6/1967 | Jones | 250/44 |
| 3,788,319 | 1/1974 | Gillette | 128/214 B |
| 3,802,432 | 4/1974 | Djerassi | 128/214 R |
| 3,857,393 | 12/1974 | Rose | 128/214 R |
| 3,892,236 | 7/1975 | Djerassi | 128/214 R |
| 3,929,130 | 12/1975 | Hargest | 128/214 R |
| 3,963,613 | 12/1974 | Chibata et al. | 210/195 R |
| 3,993,560 | 11/1976 | Halpern | 210/94 |
| 4,103,685 | 8/1978 | Lupien et al. | 128/214 R |
| 4,216,770 | 8/1980 | Cullis et al. | 128/214 R |
| 4,235,887 | 11/1980 | Voorhees et al. | 424/180 |
| 4,321,918 | 3/1982 | Clark | 606/4 |
| 4,321,919 | 3/1982 | Edelson | 604/6 |
| 4,329,986 | 5/1982 | Baff | 604/4 |
| 4,350,156 | 9/1982 | Malchesky et al. | 606/6 |
| 4,398,906 | 8/1983 | Edelson | 604/6 |
| 4,428,744 | 1/1984 | Edelson | 604/6 |
| 4,464,166 | 8/1984 | Edelson | 604/6 |
| 4,479,798 | 10/1984 | Parks | 604/4 X |

FOREIGN PATENT DOCUMENTS

| | | |
|---|---|---|
| 118711 | 8/1944 | Australia . |
| 221595 | 10/1957 | Australia . |
| 975851 | 10/1950 | France . |
| 1252323 | 12/1960 | France . |
| 2426473 | 12/1979 | France . |

OTHER PUBLICATIONS

Schlechte et al., "Regulation of the Glucocorticoid Receptor in Human Lymphocytes, *J. Ster Biochem* 16, pp. 69-74 (1982).

F. Bordin, Z. Naturforsch., 29c, 630 (1974) Furocourmarin, Photosensitizing Effect on Virus-Producing Graffi Leukemia Cells; Chem. Abstr. 82,80 (1975).

(List continued on next page.)

Primary Examiner—George F. Lesmes
Assistant Examiner—Nancy A. B. Swisher

[57] ABSTRACT

A method and system are disclosed for externally treating human blood, with the objective of reducing the functioning lymphocyte population in the blood system of a human subject. According to the method, blood is withdrawn from the subject and passed through an ultraviolet radiation field in the presence of from about 1 nanogram to 100 micrograms per ml of blood, of a dissolved photoactive agent capable of forming photoadducts with lymphocytic-DNA, mobile hormonal receptors or antigen sites to thereby effect covalent bonding between the photoactive agent and the same, thereby inhibiting the metabolic processes of the lymphocytes or complexing them; and thereupon returning the irradiated blood to the subject. The withdrawn blood may be formed into an extracorporeal stream and flowed through a treatment station whereat the irradiation is effected, as for example by exposure to UV radiation; and such flow process may be conducted on a continuous basis. If desired, at least portions of the treated blood may then be separated, as for example, by a continuous centrifuge, before returning the remaining diverted blood to the subject.

9 Claims, 5 Drawing Figures

OTHER PUBLICATIONS

Diamond et al., Photodynamic Therapy of Malignant Tumors," *Lancet*, pp. 1175–1177 (12/2/72).

Gailani et al., Specific Glucocorticoid Binding in Human Hemopoietic Cell Lines and Neoplastic Tissue, *Cancer Research* 33, 2653–2657 (1973).

Davies et al., "Corticosteroid-Induced Differential Regulation of Beta-Adrenergic Receptors . . . ", *J. Clin. Endocrin. & Metab.* 51, 599–605 (1980).

Cooperman, "Photolabile Antibiotics as Probes of Ribosomal Structure and Function", *Ann. N.Y. Acad. Science* 346, 302–323 (1980).

Lippincott, J. B. *Handbook of Experimental Immunology*, D. M. Weir and Co., 1978, pp. 15.1–15.30.

Fitzpatrick (ed) *Sunlight & Man* Chapter 22, University of Tokyo Press 1974.

Murphy et al., "Flow Cytofluorometric Analysis of Insulin Binding and Internalization by Swiss 3T3 Cells," *Cytometry* 2, 402–406 (1982).

Schechter et al., "Fluorescent Labeling of Hormone Receptors Inviable Cells" *Pro Natl Acad. Science* (USA) 75, No. 5, 2135–2139 (1978).

Mosely et al., "Targeted Killing of Cultured Cells by Receptor-Dependent Photosensitization", *Pro Natl Acad. Sci.* (USA) 78, No. 9, 5717–21 (1981).

J. A. Parrish, Photochemotherapy of Psoriasis, New Engl. J. Med., 211, 1209 (1974).

G. Lischka et al., Effects of 8-Methoxypsoralen and UVA on Human Lymphocytes, Arch. Derm. Res., 259, 293 (1977).

F. Carlassare et al., Z. Naturforsch., 33, 92 (1978).

Fox, J. L., "Synthesis of Drug Sheds Light on Its Efficacy," *Chem. & Eng. News*, pp. 25–27 (10/18/82).

Leserman et al., "Targeting to Cells of Fluorescent Liposomes Covalently Coupled with Monoclonal Antibody or Protein A" *Nature* 288, 602–604 (1980).

Martin et al., "Immunospecific Targeting of Liposomes to Cells," Biochemistry 20, pp. 4229–4238 (1981).

E. Heilmann, Extracorporeal Irradiation of Blood with 137 Caesium in Experimental Research & Clinical Application, Laser & Electroptik, 10, 18 (1978).

M. A. Pathak et al., Metabolism of Psoralens, J. Invest. Derm., 62, 347 (1974).

M. Schneider, Einfuhrunk in die Physiologie des Menschen, Springer Verlag, Berlin-Heidelberg-N.Y. (1966) at pp. 26–29, 150.

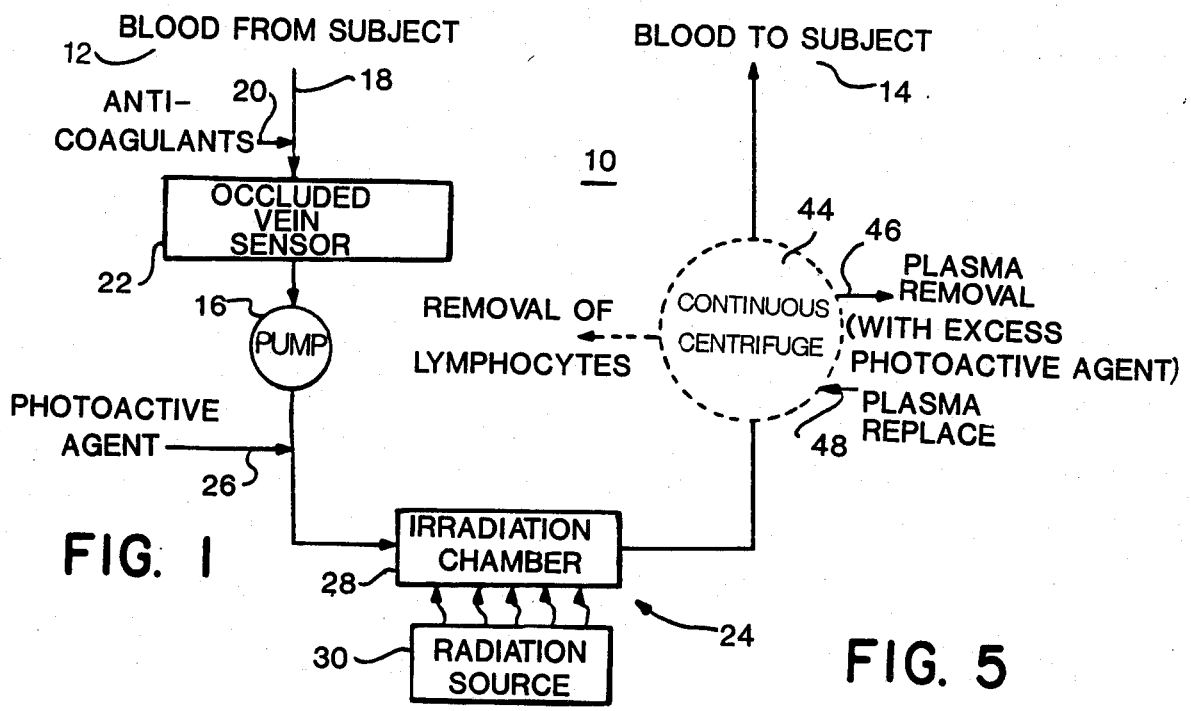
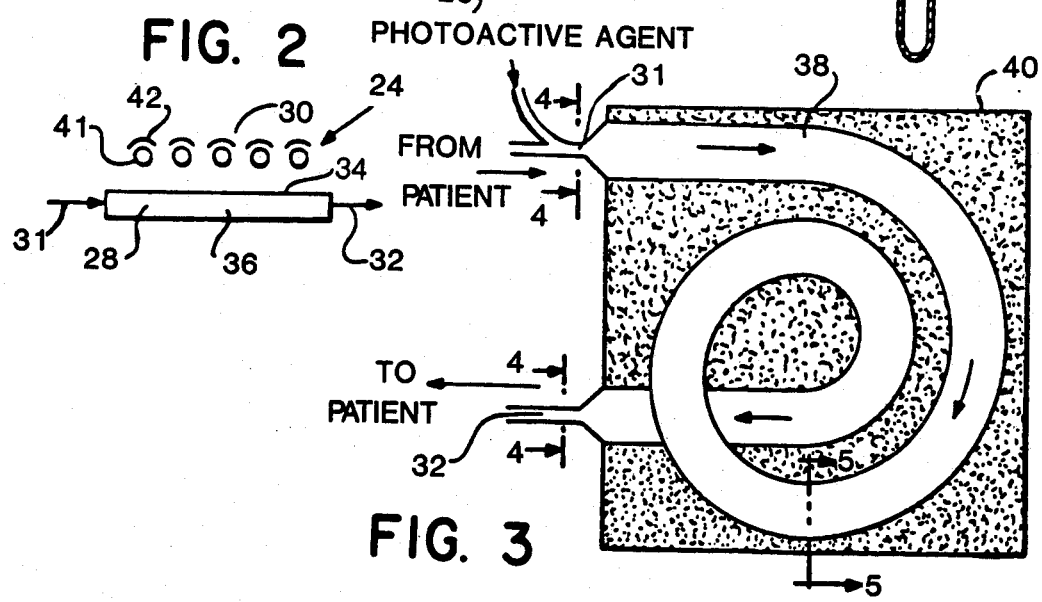

METHOD AND SYSTEM FOR EXTERNALLY TREATING THE BLOOD

This application is a continuation-in-part of application Ser. No. 274,319, filed June 16, 1981, and of application Ser. No. 272,981, filed June 12, 1981, which is a continuation-in-part of application Ser. No. 102,553, filed Dec. 11, 1979, now U.S. Pat. No. 4,321,919.

This invention relates generally to a method and system for medical treatment of a living mammal, and more specifically relates to a method for treating the blood supply of a living subject with photoactive chemical agents which when activated form photoadducts with blood constituents for the purpose of reducing the functioning population of those constituents in the blood supply of the subject.

The method of this invention has particular applicability in a number of highly significant diseases, including certain forms of leukemia, where the population of certain types of leucocytes, including especially lymphocytes, increase inordinately in comparison to the other populations of nucleated cells. While the excessive population of such lymphocytes represents a result of, rather than the underlying cause of the disease, the excessive lymphocyte population brings direct adverse effects to the patient if steps are not taken to reduce same. Complications thus rapidly develop which impair the functioning of bodily organs, and eventually a life-threatening situation is presented.

It should also be appreciated that an excessive increase in the lymphocyte population of the blood supply can occur in other human maladies, in addition to lymphocytic leukemias. Thus, for example, such results can obtain in consequence of severe allergic reactions to administered agents, including drugs or the like, or in many other lymphocyte-mediated diseases. One group of diseases which is particularly amenable to amelioration by the method of the present invention is the autoimmune diseases. Such diseases include rheumatoid arthritis, chronic thyroiditis, hemolytic and pernitious anemia and the collagen vascular diseases. These diseases result from a failure of the host's lymphocytes to recognize and tolerate as "self" tissue antigens which first arise in the host during fetal and neonatal life. Rather, the host lymphocytes react to these normally benign antigens as foreign, and multiply so as to form sensitized clones which express antibody-like surface receptors structured so as to bind the challenging antigens. The present invention provides a method which may be adapted to eliminate these abnormally-activated lymphocytes from the blood of the afflicted host.

In addition to the development over the years of pharmaceutical agents and the like, which may non-specifically reduce the lymphocyte population, e.g., by altering the underlying production rate of same, various techniques have from time to time been used in an effort to directly attack the problem, as for example, by mechanically removing such lymphocytes from the blood supply. It is thus known, for example, to pass the blood supply through a continuous centrifuge, whereby one seeks to selectively remove lymphocytes to reduce the population of the latter in the processed blood supply. In general, however, this method tends to be very inefficient, in part because the density differences between the blood fractions including the undesired lymphocytes and fractions which include desired blood components, is insufficient to assure that high percentages of the former are removed while retaining high proportions of the latter.

It is also well-known to treat diseases such as leukemia with high energy electromagnetic radiation, including that in the x-ray region. While such treatment is often directed at internal bodily organs in which the blood cells are being generated, it has also been known to irradiate the blood supply with x-radiation at a point external to the body (the blood having first been withdrawn), whereby the radiation is not rendered directly incident on the body or internal organs of same. This method, while powerful, is indiscrimate, in that the intensely disruptive energy, in addition to destroying undesirable cells, disables or destroys components of the blood which are desired to be retained in vital status.

Among the pharmaceutical agents used to treat the excessive lymphocyte population resulting from leukemia are agents which are active against the lymphocyte itself. Cortisone is one such agent. Its effectiveness, however, is limited as it does not completely suppress the aberrant metabolic activity of the malignant lymphocyte. The mechanism by which cortisone acts on lymphocyte cells is not fully understood. It is believed, however, to initially bind specifically to the cortisone receptors in the lymphocyte and to be carried by these mobile receptors to the cell's nucleus wherein it acts to alter the metabolic activity of the cell.

However, cortisone and its derivatives are not specific for lymphocytes, and serious side effects in other tissues are frequent complications of such therapy. For example, diabetes mellitus, hypertension, and demineralization of bones often occur and limit classical cortisone therapy.

Certain other chemical agents are known or are believed to weakly bind to the nucleic acids of certain nucleated cells where they intercalate by forming molecular complexes involving low energy chemical interactions or intermolecular attractions, which generally are transient and insufficient to significant affect the rate of DNA synthesis in the cell. The "psoralens" which are described in U.S. Pat. No. 4,321,919 are such chemicals.

Certain ligating proteins, known as antibodies, are also active against lymphocytes. The interaction of an antibody with a particular lymphocyte requires that the lymphocyte have a site or antigen which is geometrically and chemically receptive to a corresponding active site on the antibody. The forces which bind an antibody to an antigen consist of attractive forces including hydrogen bonding, apolar bonding, ionic interactions and Van der Waals interactions, the strength of which are inversely proportional to the distance between the interacting groups. Accordingly, any structural variations in the lymphocyte membrane which serve to alter the geometry of the antigen can serve to prevent the binding of an antibody to the antigen. Further, once an antibody binds to an antigen on a cell, the cell may undergo "antigenic modulation," altering its cell membrane so that antibodies can no longer bond to it. Where a lymphocyte's membrane has a structure which blocks the antibody from its antigenic site, the antibody while still attracted to the antigen will be unable to form any linkage of a permanent nature. Inasmuch as variations in cell structure are more the rule than exception with malignant and activated cells, and "antigenic modulation" is a frequent occurrence, it is often not possible to effectively combat leukemic or activated cells with simple antibody administration.

The use of antibodies to permanently inactivate or remove immunogenic chemicals which may be found in the blood, such as undesirable natural antibodies, has also been hindered by the inability of an antibody to irreversibly or strongly complex with antigens.

An improved technique for combating human cancers involves the use of monoclonal antibodies which are specific for the antigens expressed by a given tumor cell. For example, human lymphoma cells have been fused to normal human lymphocytes to increase the production of the antigen. The fusion product was injected into a mouse, which responded by producing an antibody to the lymphoma antigen. The mouse's antibody producing spleen cells were then fused with mouse myeloma cells to make a hybridoma that synthesized a specific antilymphoma antibody which could be used to combat the lymphoma cells present in the human patient. See Y. Baskin, *Technology Review* (Oct. 20, 1982) at page 19, and U.S. Pat. Nos. 4,172,124 and 4,196,265.

The above-described pharmacologic interactions can be strengthened by use of photoactive chemical agents which comprise photocytotoxic agents or having one or more functional groups which are excited by incident ultraviolet radiation and which when so activated have a tendency to form covalent linkages with nearby chemical groups. The reactivity of various photoactive agents varies from the chemically specific, which is the case with agents such as the psoralens and the anticancer drug bleomycin, to agents having great reactivity toward virtually any group, which is the case with diazo and azide groups. The diazo and azide groups are the preferred photoactive functional groups for imbuing normally photoinactive chemical agents to be used in the invention with the photoactivity which is essential in the method of this invention.

Until the present invention, photoactive chemical agents have been utilized therapeutically only in very limited fashions. On a clinical level, one class of photoactive compounds, the psoralens, have been used to treat patients suffering from psoriasis. Other uses of these agents have been almost exclusively experimental investigations of cell physiology and chemistry, typical reports of which appear in the following articles in the *Annals of N.Y. Acad. Sci.*, 346, "Photoaffinity Probes in the Antibody Combining Region", Richards, F. F. and Lifter, J., pp. 78–89; and "Photolabile Antibiotics as Probes of Ribosomal Structure and Function", Cooperman, B. S., pp. 302–323.

BRIEF DESCRIPTION OF THE INVENTION

In accordance with the present invention, a method has been found which enables safe and effective reduction of the functioning population of certain blood constituents. More particularly, the method of the present invention enables the reduction of the functioning population of certain nucleated cells and undesirable antigenic chemical substances, such as undesirable autoreactive antibodies, in the blood supply of a human subject.

According to the method of invention, blood requiring such treatment is withdrawn from the subject and irradiated with UV radiation in the wavelength range of from about 2000 to 4000 Angstroms, and preferably, from about 3200 to 4000 Angstroms, in the presence of an effective amount of a dissolved photoactive chemical agent of the type capable of intermolecular or chemical association with certain receptor sites. As used with respect to the practice of the present invention, the term "receptor sites" refers to:

(1) the nucleic acids of nucleated blood cells,
(2) the molecule receptor sites of nucleated blood cells,
(3) the antigenic sites on nucleated blood cells, or
(4) the antigenic sites on immunogenic chemicals.

Upon irradiation, the photoactive chemical agent is induced to form a permanent photo-adduct with a receptor site in or on the nucleated blood cell or immunogenic chemical whereby the destruction or inactivation of the adducted constituent is assured. The irradiated blood is then returned to the subject.

When a photoactive chemical agent having an affinity for the nucleic acid of nucleated cells such as lymphocytes is employed in the present invention, the aforementioned intermolecular attractive forces draw the agent into an intercalated relationship with the nucleic acids of the lymphocytes. Prior to activation, the agent has little or no effect on the cell chemistry. However, upon irradiation the agent forms certain covalent attachments or otherwise complexes with the nucleic acids of the cell, thereby inactivating the nucleic acid chains and inhibiting the metabolic functions of the cell. In this fashion, the cell's processes having been disrupted, and in particular its ability to divide prevented, inactivation or death of the cell results.

DETAILED DESCRIPTION OF THE INVENTION

The family of chemicals known in the art as the psoralens and more fully described in U.S. Pat. No. 4,321,919, the disclosure of which is incorporated herein by reference, have been found to have the activity described and are deemed well suited for application in the present invention. Photoactive chemical agents, having an affinity for DNA, such as the psoralens, when used in the invention have a highly desirable benefit in that the impairment and destruction of lymphocytes tends to be selective, in certain diseases such as leukemia, to the cells most sought to be reduced, by virtue of the fact that it is such cells which are undergoing the most intense metabolic activities to begin with, whereby they are the cells most subject to disablement by the present process.

Cortisone is a chemical agent having an affinity for particular receptors within the nucleated lymphocyte cell. As has been previously indicated, cortisone's applications in reducing the functioning lymphocyte population in patients suffering from leukemia or autoimmune diseases have been less than entirely satisfactory. According to the present invention, however, cortisone can be utilized to treat leukemic or activated lymphocytes in a new and far more effective fashion.

Prior to application in the invention, cortisone must first be rendered photoactive ("photocytotoxic"). Those skilled in the art will appreciate that the photoactivation of cortisone or a similar steroidal hormone can be achieved using established chemical techniques. The particulars of that chemistry are not deemed to be within the scope of this invention, which is limited to a method whereby certain chemical agents can be employed to achieve previously unattainable reductions in the functioning population of certain blood constituents. Those skilled in the art will also recognize that employing established chemical procedures, including where necessary that of binding site protection, cortisone can be substituted with a photoactive moiety at several positions, the substituted cortisones can be evaluated and the homologue retaining the largest percentage of cortisone's normal biological activity easily determined. The chemistry of steroid hormone photoactivation and the determination of most active homologue is thoroughly discussed in the following articles:

(1) J. A. Katzenellenbogen, H. N. Myers and H. J. Johnson, Jr., *J. Org. Chem*, 38, 3525-33 (1973).

(2) J. A. Katzenellenbogen, H. J. Johnson, Jr. and H. N. Myers, *Biochemistry*, 12, 4085-92 (1973).

(3) J. A. Katzenellenbogen, H. J. Johnson, Jr., K. E. Carlson and H. N. Myers, *Biochemistry*, 13, 2986-94 (1974).

As these articles disclose, the photoactivation of steroids has been achieved with great success through their substitution with the photoactive moieties known as diazo and azide groups. These groups individually have a high degree of intrinsic photoactivity and that activity is retained when they are incorporated into another chemical agent, thereby rendering it photoactive.

Employing then, known techniques of photoderivatization, the 16-diazocortisone, which is preferred in the invention for retaining a high degree of its original pharmacological activity, can be synthesized in good yield by first nitrosating cortisone to give 16-oximocortisone, which can be converted into the 16-diazocortisone by chloramine oxidation. Other substituted cortisones may be derived by the nitration of cortisone using nitric acid in glacial acetic acid. The products of this nitration step are a number of azide derivatives, which can easily be separated by column chromatography. The reaction parameters employed to make these products can be found in enabling detail in the aforementioned Katzenellenbogen article in *J. Org. Chem.*, 38, 3525-33.

Photo-derivatized cortisone, having the preferred structure disclosed above or one of the other possible less preferred homologues, upon addition to the blood, readily enters the lymphocytes or other nucleated cells and associates itself with the cortisone receptor sites in those cells. The cells are thereby photosensitized, in that they may be strongly affected by irradiation with ultraviolet light. After a suitable interval, calculated to allow a high percentage of the substituted photocytotoxic cortisone to reach these receptor sites, typically in the range of 1 minute to 2 hours, and preferably 5-15 minutes, the blood containing a dosage of dissolved photoactivated cortisone that approximates that conventionally used in cancer or immunosuppressive treatment, typically in the range of from about 1 nanogram to 100 micrograms per ml of blood, is irradiated with UV radiation. Irradiation of the blood activates the photoactive moiety on the cortisone molecules in situ at the cortisone receptor sites and causes the formation of photo-adducts between the substituted cortisone and the cortisone receptor, as a consequence of which the receptor's ability to transmit cortisone vital to the continued metabolic activity of the cell is destroyed. Accordingly, a very large fraction of the cortisone receptors in the lymphocytes having been inactivated, the cells quickly become unable to function, and most particularly to divide, and their inactivation or destruction rapidly follows.

The following additional chemical photoactive agents are known to interact directly with intact cells following exposure to UV and visible light so as to cleave or otherwise deactivate cellular DNA. The following references, the relevant portions of which are incorporated by reference herein, disclose photocytotoxic agents which may also be useful in the practice of this invention.

(1) Ethidium and acridines (Yielding K. L. and Yielding L. W.: Photoaffinity labeling of DNA, *Annals of N.Y. Acad. Sci.*, 346, 368-378 (1980); Y. K. Ho et al., *Blood*, 52, 1099-1114 (1978)—Also adriamycin, daunomycin, rubidazone).

(2) Sulfonamides, sulfonylureas, phenothiazines, tetracyclines, coal tar derivatives, pyrenes, anthracene, pyridine, phenanthrene (Kornhauser A.: Molecular aspects of phototoxicity, *Annals of N.Y. Acad. Sci.*, 346, 398-414 (1980)).

(3) Specifically reactive antibodies (Richard F. F. and Lifter J.: Photoaffinity probes in the antibody combining region, *Annals of N.Y. Acad. Sci.*, 346, 78-89 (1980)).

(4) Transition metal, i.e., copper, iron and cobalt complexes of bleomycin, deglycobleomycin or DNA-active derivatives thereof. (J. L. Fox: Synthesis of Drug Sheds Light on its Efficacy, *Chem. and Eng. News*, Oct. 18, 1982, p. 25).

(5) Organoplatinum anticancer drugs. (A. L. Zwelling and K. W. Cohn, in *Principles of Cancer Treatment*, B. Chabner, ed., Saunders Pub. (1982) at pages 309-339).

(6) Pyrene cholesteryloleate. (S. T. Mosley, et al., *Proc. Natl. Acad. Sci. USA*, 78, 5717-5721 (1981)).

(7) Prophyrin derivatives. I. Diamond, et al., Lancet, 3, 1175—1177 (1972)).

Antibodies specific to particular blood constituents can be generated but, as has been indicated, it has not been possible to employ them with good results in reducing the population of malignant cells in the blood because of the variations in structure which are common with malignant cells and cellular phenomena such as antigenic modulation which enables cells to become resistant to specific antibodies. Thus, for example, antibodies specific for a particular type of malignant T-lymphocyte may be unable to complex with a large fraction of cells of that type in the blood, regardless of the antibodies normally having an affinity toward those cells, and a significant number of lymphocytes having been complexed by the antibodies shed their bound antigens breaking the antibodies' hold on them. According to the present invention, however, photoactivated antibodies can be utilized to reduce the functioning lymphocyte population to a previously unobtainable degree, by preventing antigenic modulation. Moreover, employing the method of the present invention photoactived antibodies specifically reactive to other blood constituents such as undesirable antibodies generated by circulating malignant cells, can also be employed to reduce the population of those constituents in the blood with similar great effectiveness.

The methods whereby an antibody specific for a particular cell or immunogenic chemical may be produced and purified are well knwon in the art and have been generally discussed hereinabove. Suffice it to say that large quantities of very specific monoclonal antibodies can be made by hybridoma or by other established techniques.

The chemical techniques whereby an antibody desired for use in the present invention may be rendered photoactive are also well known to those skilled in the art. It will also be obvious to those skilled in the art that virtually all antibodies have a number of sites suitable for photoactive derivation. Methods whereby moieties foreign to an antibody may be added thereto without injuring the antibodies' ability to complex with its specific antigens, for example, have been disclosed in the *Handbook of Experimental Immunology*, Weir, D. M., publ. J. B. Lippincott, 1978, pp. 15.1–15.30. In furtherance of the objectives of this invention, it is important that the process of derivatization not destroy the combining region of the antibody which is specific for the target cell. In this regard, it should be noted that in view of the number of potential sites for derivatization on most antibodies and the many different techniques whereby they may be substituted with a photoactive moiety, such as the preferred diazo and azide groups, it will rarely be necessary to take the precaution of specifically protecting the combining region. Where, however, it is found that the combining region on an antibody would otherwise be destroyed by the photoderivatization of that antibody, established techniques of combining site protection and subsequent removal of the protecting group can be employed.

When photoactivated antibodies specifically reactive to some blood constituent, which for example, in a preferred embodiment of this invention might be the malignant T-lymphocytes of a patient, are added to that patient's blood in the method of the present invention, they will very quickly complex with T-lymphocytes for which there exists the required correspondence of antibody combining region and cell antigenic site. Numerous antibodies, however, by reason of deficiencies in their own combining regions or in their target cells' receptors, while attracted to the target lymphocytes, will be unable to form an antibody-antigen complex that will lead to the inactivation or destruction of the cells. Upon irradiation with UV radiation of a wavelength capable of activating the particular photoactive moiety which has been attached to the antibodies, the photoactive moieties on the antibodies which have complexed will preferentially form photo-adducts with the complexed cells, thereby permanently binding them to their complexed antigenic antibody and eliminating antigenic modulation as a means whereby the complex can be broken. Other antibodies which had previously failed to effectively complex with any of the target cells to which they were attracted because of insufficient correspondence in their respective binding regions, will upon photoactivation preferentially form photo-adducts with those cells, thereby creating a photo-adduct complex where none had existed before. In the described fashion, dosages of photoactivated antibody approximating those conventionally employed in the treatment of maladies, in the order of from about 1 nanogram to 100 micrograms per ml of blood, can be applied thereto with therapeutic effectiveness.

The aforedescribed photo-induced antibody-antigen complexing is amplified by the introduction of multiple photoactive groups into the antibody structure, for the presence of several photoactive moieties on the antibody increases the likelihood that a single antibody will be able to complex with more than one target cell. When such antibodies are employed according to the method of the invention, they have an enhanced tendency to form networks or chains of complexed cells which can be removed from the blood with particular facility.

It is also within the scope of this invention that antibodies specific to particular undesirable natural antibodies or other immunogenic chemicals can be rendered photoactive and used according to the method of the invention to form complexes which strongly bind those chemicals, enabling their removal from the body with a far greater efficiency than previously possible.

The photoactive chemical agents useful in the practice of the present invention may also comprise a carrier moiety which is selected to enhance the delivery of any of the above-described photocytotoxic cell-eliminating agents into effective proximity to the target cells. Carriers useful in combination with the agents described hereinabove are selected from those which possess a strong affinity for receptors on or within target cells such as sensitized T-lymphocytes or other nucleated blood cells. The photocytotoxic agents are physically incorporated within, or chemically bound to, the carrier moieties which, when introduced into the extracorporeal blood stream of the affected patient, act so as to carry the photocytotoxic agents into close proximity to the target cell. Irradiation of the blood stream as described herein then activates the agents so as to interfere with the metabolism of the target cells.

Activated T-lymphocytes and other nucleated blood cells have been shown to express receptors specific for a variety of polypeptides which act to effectuate the lymphocytes' metabolic demands when bound thereto. This specificity can be utilized to eliminate undesirable cell populations by a technique which may be termed "receptor-dependant photosensitization". For example, receptors for natural and biosynthetic insulin have been identified on activated T-lymphocytes. The polypeptides interleukin, transferrin and thymopoietin also have been demonstrated to exhibit a strong affinity for activated T-lymphocytes which has been attributed to the presence of specific receptors. It is a part of the present invention to utilize new photoactive chemical agents prepared by covalently linking these lymphotropic polypeptides to molecules which will interfere with lymphocytic metabolism when activated by UV light. Such molecules have been described herein above, and may be termed cell-photosensitizing agents or photocytotoxins. The polypeptide binding region will readily associate with the lymphocyte receptor, thus internalizing the cell photosensitizing agents within the lymphocytes sought to be destroyed while avoiding destruction of normal lymphocytes.

Methods have been developed for linking photocytotoxic dyes to insulin which would be expected to be generally useful for linking a wide variety of cell-photosensitizing agents to insulin, interleukin, transferrin, or thymopoietin. For example, the epsilon-amino group of lysine B-29 of insulin has been derivitized with m-maleimido-benzoyl-N-hydroxysuccinimide ester and coupled with a rhodamine derivative of alpha-lactalbumin (an inert protein) via a free thiol group on the protein moiety so as to form a disulfide bridge. The binding efficiency and biological activity of the modified insulin was substantially retained. Y. Shechter, et al., *Proc. Natl. Acad. Sci, USA*, 75, 2135–2139 (1978). Fluorescein-isothiocyanate-labeled insulin is commercially available from Sigma (St. Louis, Mo.) and has been demonstrated to be rapidly internalized into cell lyosomes by R. F. Murphy, et al., *Cytometry*, 2, 402 (1982). Analogous chemical linking reactions would permit the formation of insulin, interleukin, transferrin or thymopoietin derivatives of other cell-photosensitizing agents such as bleomycins, psoralens, corticosteroids, phorphrins, pyrenes, acridines, organoplatinums, and the like.

These photoactive agents would be introduced into the extracorporeal blood stream of a patient and the lymphocyte-agent complexes irradiated as described hereinbelow to effectuate elimination or reduction of the targeted cell population. Alternatively, phototoxic dyes themselves, such as rhodamine and fluorescein, can be delivered to target cells and irradiated.

Another technique for receptor-dependent photosensitization of target cells involves the use of liposomes with lymphotropic polypeptides or with antibodies, preferably monoclonal antibodies, covalently attached thereto. Liposomes are spherical phospholipid bilayer vesicles. Liposomes may be prepared having useful diameters in the range of 500 angstroms-0.5 micrometers and may be loaded with effective amounts of cell-photosensitizing chemicals such as dyes, steroid derivatives and other anticancer drugs. Methods such as those disclosed by J. N. Weinstein et al., *Ann. N.Y. Acad. Sci*, 308, 433 (1978), the disclosure of which is incorporated by reference herein, may be employed to load liposomes with any of the photocytotoxic agents disclosed hereinabove. The lipid starting materials may be derivatized with antibody or polypeptide either before, or preferably after, the lipids are incorporated into the liposome wall. Thiol groups on the antibody or polypeptide molecules are linked via disulfide bridges to pyridyldithiopropionyl-derivitized lipids such as phosphatidylethanol amine and the substituted lipids formed into liposomes which encapsulate photocytotoxins by the procedures of F. J. Martin, et el., *Biochem.*, 20, 4229 (1981); *J. Biol. Chem.*, 257, 286 (1982); and L. D. Leserman, et al., *Nature*, 288, 602 (1980), the disclosures of which are incorporated by reference herein.

When introduced into the extracorporeal blood stream by the procedures discussed hereinbelow, the polypeptide- or antibody-bound liposomes attach themselves to, and are absorbed by the lymphocytes which possess surface antigen or receptor sites for the particular antibody or polypeptide employed. The liposomes are lysed by intracellular enzymes, and the encapsulated cell-photosensitizing chemicals are released. Alternatively, the liposomes become fused with and incorporated into the cell membrane.

Irradiation of the bloodstream with UV light deactivates the photosensitized cells by effecting disruption of cellular metabolism as discussed hereinabove.

According to the method of the present invention, regardless of the type of photoactive chemical agent employed therein, blood withdrawn from a subject for treatment can be handled in batch form, but preferably is formed into an extracorporeal stream and passed through a treatment station whereat the irradiation is effected. Such a treatment station may take the form of an extended flattened tubular passageway, the walls of which are substantially transparent to the incident ultraviolet light (UV) used to activate the photoactive chemical agent. Typical cumulative radiation doses range from about 0.1 to 100 joules per $cm^2$ and preferably from about 5 to 60 joules per $cm^2$ of blood surface whether the process is carried out on a continuous or discontinuous basis, and typical flow rates through the irradiation station can be in the range of from about 10 to 75 ml/min.

Following treatment, the entire batch, or irradiated flow of diverted blood, can be returned to the patient. However, depending on which photoactive chemical agent was employed in the treatment of the blood, it may be preferable to filter dialyze or centrifuge the treated blood prior to its return to the patient. The instances in which such treatment would be deemed appropriate are more fully elucidated in the detailed description of this invention.

BRIEF DESCRIPTION OF THE DRAWINGS

The invention is diagrammatically illustrated, by way of example, in the drawings appended hereto, in which:

FIG. 1 is a schematic flow diagram illustrating a preferred embodiment of a system operating in accordance with the present invention;

FIG. 2 is a schematic elevational view of the irradiation station portion of the FIG. 1 system;

FIG. 3 is a plan view, schematic in nature, of one embodiment of the irradiation station of FIG. 2; and FIGS. 4 and 5 are cross-sectional views, taken along the lines 4—4 and 5—5 of FIG. 3, and illustrate the configurations of the flow passageway and the output passage for the FIG. 3 device.

DESCRIPTION OF PREFERRED EMBODIMENT

In FIG. 1 herein a schematic diagram appears of a system 10 in accordance with the present invention. Except for the irradiation station, the bulk of the components of system 10 are per se conventional and known in the art; and hence it is not deemed appropriate or necessary to vastly detail same.

As indicated in the Figure, blood may initially be withdrawn from the human subject, as at 12. Typically the blood is withdrawn via a donor needle, which may, e.g., be emplaced at the right antecubital vein. In the showing of FIG. 1, it is assumed that the processing of blood pursuant to the invention is conducted on a continuous basis, i.e., for purposes of the present discussion the flow may be regarded as continuous from withdrawal at 12, to final return of the blood to the subject at 14. Such return 14 is typically effected via a recipient needle positioned in the left antecubital vein. Where the flow is indeed continuous in this manner, a typical blood flow utilizable in practice of the invention is in range of from about 10 to 75 ml/min. with a more preferred range being from about 40 to 50 ml/min. The indicated flow rates are effected by means of a pump 16, which is positioned in the extracorporeal blood flow stream generally indicated at 18, and may comprise one of numerous types of pumps used for blood flow treatment purposes, including such pumps as those available from Haemonetics Corp. under Model Designation 30.

As is known in the pertinent medical art, anti-coagulants are preferably injected into the extracorporeal blood flow stream at 20, i.e., close to the point of blood withdrawal. Such anti-coagulants can comprise solutions of acid citrate dextrose and/or of heparin, or of other known compositions useful for this purpose.

An occluded vein sensor 22 is preferably provided in stream 18 for purposes, as known in the art. Such sensor basically comprises a reservoir or buffer volume, the object of which is to prevent or inhibit generation or continued existence of bubbles in the blood flow stream.

Pursuant to a preferred mode of practicing the present invention, the photoactive chemical agent is preferably added to the blood of the human subject external to such subject; and thus as shown in the system 10 of FIG. 1, may be provided to the flowing blood downstream of pump 16, and just upstream of where the blood enters the irradiation station 24.

The basic technique used in introducing photoactive chemical agents, is to dissolve or mix same in an isotonic solution, which thereafter is directly injected into the flowing blood streams, as at 26. The agents are injected at a rate in comparison to the blood flow rate as to achieve a concentration in the blood thereafter passed to irradiation station 24 in a desired effective range for each of the chemical agents of the invention.

In the foregoing connection it should be appreciated that the primary objective of the operations thus far described is one of achieving the desired concentration of the photoactive chemical agent prior to introduction of the blood to the irradiation station. In accordance with a further aspect of the invention, it will therefore be appreciated that the said photoactive agent need not necessarily be directly introduced by injection into the extracorporeal blood stream 18 flowing in FIG. 1. Rather, it also may be acceptable to achieve the desired concentration of photoactive agent by orally or otherwise administering the compound directly to the patient. Where, for example, pursuant to the invention, psoralen is orally administered, it can be provided in oral dosages of from about 0.6 to 1.0 mg per kg of body weight. The desired concentration range in the blood used for practice of the invention, is then achieved in about two hours from oral administration. Alternate modes of administration for the other photoactive chemical agents within the scope of this invention and the doses appropriate therefor will be apparent to those skilled in the art.

However, it is preferred to introduce the photoactive chemical agents of the invention to the extracorporeal stream (or to an extracorporeal batch volume) in order to achieve more exact concentration levels; and further, to avoid or minimize possible said effects and the like, which can occur from administration of any drug directly to the body system.

At irradiation station 24, consisting of an irradiation chamber 28 and radiation source 30, the blood now carrying in solution the desired concentration of photoactive chemical agent, is subjected to ultraviolet radiation (UV) and preferably UV radiation having the bulk of its spectral components in the preferred range for the activation of the particular photoactive agent being employed in the treatment being conducted. The materials of construction of the irradiation station 24 are selected so as not to block radiation in the desired portion of the UV spectrum.

In FIG. 2, a schematic elevational view appears of an irradiation station 24 of a type suitable for use with the invention. Such station consists of a blood treatment or irradiation chamber 28, having an inlet 31 and an outlet 32, enabling blood flow through the chamber, and a spaced source 30 for UV radiation. The chamber 28 can take various forms, with the principle requirement for same being that the wall 34 of same opposed to source 30, be substantially transparent to the incident UV radiation. The said chamber (or at least wall 34) can therefore typically be comprised of various substantially UV-transparent plastics, as are commonly used in tubing constructed for administration of standard intravenous solutions, such as polyvinyl chloride and the like.

In one preferred embodiment of irradiation chamber 28, which is easily adapted for use in both the continuous and batch modes of this invention, the device comprises a simple envelope which is irradiated from above and below. Accordingly, in this embodiment, the blood to be treated flows through irradiation chamber 28 in central void 36 which is substantially of thin rectangular cross-section. The surface area of the chamber 28 is adapted in conjunction with the light sources so as to provide the blood contained therein within the desired radiation dose level. In an alternate embodiment, blood treatment chamber 28 has a configuration as shown in FIGS. 3, 4, and 5. In this instance a tubular coil 38, which in cross-section (FIG. 5) is flattened to a very elongated elipse, is fixedly maintained in or upon a support plate 40. The blood flow inlet 30 to the coil is of circular cross-section, and in terms of FIG. 1 is at a point downstream of pump 16. The feed-in for the photoactive chemical agent is schematically depicted at 26. The highly flattened cross-section of the coil enables good flow for the blood passing through the coil, but more importantly, enables good exposure of the flowing blood to the incident UV radiation. The outlet 32 is again returned to a circular cross-section.

Regardless of the design selected for the chamber 28, it is preferred that the chamber be as thin as practicable. Chambers having a thickness in the range of from about 0.05 to 10 mm are within the range contemplated in the invention with chamber thicknesses in the range of from about 0.05 mm to 1 mm preferred.

UV source 30 may comprise one or a plurality of side-by-side or otherwise arranged UV light sources 41, each of which may be backed by a reflector 42. The UV sources can comprise commercially available lamps, numerous types of which are known in the art.

By way of example, source 30 can comprise a single 1000 watt Hg lamp of the type available from Oriel Corporation of Stamford, Connecticut, under Model designation 6287. When used with appropriate filters this source provides a good relatively continuous spectrum of high intensity radiation between 3200 and 4000 Angstroms, with a peak emission at about 3650 Angstroms, which is preferred when psoralen is the photoactive agent being employed in the method of the invention. The said lamp with a suitable reflector can be positioned approximately 5 to 30 cm from chamber 28. With the flow rates utilized in accordance with one aspect of the invention, such a source will provide absorbed energy in the flowing blood within the range of interest for practicing the method of the invention.

The blood flow from irradiation station 24 proceeding as shown in FIG. 1 via outlet 32, can be directly returned to the subject at 14. Optionally, however, prior to returning the treated blood to the patient, it may be heat exchanged so as to adjust its temperature to that of the patient's circulating blood. Heat exchange as described is necessary whenever the treated blood, by consequences of its treatment, has attained a temperature substantially at variance with that of the patient.

Where the method of the invention has been employed to reduce the functioning lymphocyte population of the blood, employing either a DNA active agent, such as a psoralen, or a photoactivated cortisone, the treated lymphocytes upon return to the patient as a consequence of their treatment will be rapidly broken down and destroyed by the normal processes occurring in the patient. More specifically, by their treatment according to the aforementioned embodiments of the invention, the metabolic functions of the treated lymphocytes are impaired to the extent that with appropriate doses of photoactive agent and UV radiation a substantial percentage of the treated cells will be destroyed on a gradual basis over a period of days. A benefit of this feature of the invention is that it is thus possible to treat substantially the entire blood supply of a patient in a single treatment without causing the catastrophic overloading of the body's blood purification system which would otherwise result if the entire population of treated lymphocytes were to succumb to the treatment at the same time.

Where photoactivated antibodies specific to a malignant lymphocyte are employed in the other preferred embodiments of the invention, the blood returned to the subject will have its lymphocytes (or alternatively an undesirable antibody) complexed by the activated antibody and thus tagged for removal from the blood stream. Since, however, the photoactivated antibody complexes formed according to this embodiment of the invention are essentially completely formed prior to the exiting of the blood from the irradiation station 24, the blood must either be dosed, with relatively small amounts of activated antibody so as not to shock or overload the patient's biological blood filtration system, or the treated blood must be filtered, dialyzed or centrifuged prior to its return to the patient.

Regardless of which photoactivated agent is employed in the invention or at what rate it is administered, the burden placed upon the body's organ system can be further alleviated by utilizing in conjunction with the present system, a continuous centrifuge 44 (or other filtration system), which device serves several functions.

It is to be noted that continuous centrifuges of the type here utilized, have been long employed in blood flow processing systems commercially available from several manufacturers, including Haemonetics Corporation of Braintree, Mass., and the IBM Corporation, Medical Products Division, of Monsey, N.Y. In the prior art systems in which such devices have been utilized all elements of FIG. 1 have been present, with the singularly important exception of the irradiation station 24. The function of the continuous centrifuge in such prior art systems has been one of separating excess lymphocytes or other blood components of interest. Where so used, a detriment of such system was the inefficiency of same, i.e., the centrifuging process can at best remove about 40 to 50% of the lymphocytes, and unfortunately, also removes components which are in fact desired to be retained.

In the system 10 of the present invention, two functions can be performed by the continuous centrifuge 44. One of these, is removal of lymphocytes or other complexed blood constituents, as previously discussed. Because the present invention in its treatment embodiments relies primarily on impairment of function of the lymphocytes to ultimately reduce the functioning population of same, the centrifuge 44 need not be relied upon to the extent that same has been in the aforementioned prior art arrangements. From a mechanical viewpoint, this implies that one need not work as close to the specific gravity interface between the lymphocyte fraction of the blood and the desirable fractions of the blood which one seeks to retain. Thus one can avoid undue separation of those desired fractions of the whole blood.

In the embodiments of the invention employing photoactivated antibodies, the antibody complexes formed will be easily separated from the other desirable blood fractions, whether by filtration or in the depicted centrifuge type device 44.

The continuous centrifuge 44, may further be utilized for an additional important purpose. In particular, some or virtually all of the blood plasma may be removed at 46 and replaced with fresh plasma at 48. This washing technique enables one to effectively withdraw the excess photoactive chemical agent compounds which may be present in the blood plasma, replacing the plasma at 46 with isotonic fluid free of the same. Thus, when the blood is returned to the subject at 14, it is substantially free of any excess chemical agent, i.e., other than those which combined with the treated blood constituent in the manner desired.

It should also be reemphasized that, while the preferred mode of practicing the present invention as illustrated in FIG. 1 contemplates a continuous operation, the blood treatment pursuant to the invention can be effected by batched techniques. Thus, for example, a distinct, fixed quantity of blood may initially be withdrawn from the subject. Such quantity or batch, may already have present therein the desired quantities of dissolved photoactive chemical agent, i.e., by prior administration to the patient; or the said agent may be admixed externally with the withdrawn blood. The said blood batch bearing the desired agent may then be provided to an irradiation station, where the desired quantity of UV energy is rendered incident upon same. During this process the batch of blood can be flowed through the station as previously discussed, or if the quantity of blood is appropriate and the blood treatment chamber 28 of appropriate dimensions, the batch can simply be treated under static conditions until the desired energy has been dissipated. Thereafter, the treated blood is taken from the irradiation station, and either centrifuged as above discussed, or directly returned to the subject.

The following example is included to illustrate the application of the method and system of this invention in bringing about a therapeutic reduction in the functioning population of a blood constituent in a human subject's blood supply.

EXAMPLE I

Five hundred cubic centimeters of blood (500 cc) were drawn from a patient suffering from acute leukemia. This blood was held in a blood bag, and lines were run from the blood bag to the blood treatment system and then from that system back to the blood bag.

In this experiment, the system employed consisted of a pump and a multi-pass UV Exposure Station, having an exposure chamber with a thickness of 1.0 mm and a total surface area of 0.312 square meters. The exposure chamber was irradiated from above and below by ultraviolet A light sources providing radiation having the bulk of its spectral components in the 3200 to 4000 Angstrom range, with peak intensities at about 3600 to 3700 Angstroms. The level of radiation incident to the surfaces of the exposure chamber was measured at about 28.8 $J/cm^2/hr$.

A psoralen level in the blood to be treated of 100 nonograms ml was achieved by oral administration of psoralen to the patient two (2) hours prior to the taking of the blood for this test. Subsequent to taking, the blood sample was dosed with 20 units of heparin sulfate per ml of blood, in order to prevent coagulation of the blood sample in the apparatus.

The white cell count of the blood sample, prior to commencement of the test, was 500,000/$mm^3$ which level compares very unfavorably with a normal count of 5,000 cells/$mm^3$. Examination of the cells revealed that virtually all the cells in the sample were malignant T-lymphocytes.

In operation, blood was drawn from the blood bag at a rate of 40 cc/min., passed through the irradiation chamber and then returned to the blood bag. A sample was taken from the return line prior to the commencement of UV irradiation and at one hour intervals thereafter, the last sample being taken 3 hours after commencement of irradiation. The samples were maintained in cultures from which aliquots were drawn for evaluation on the third, fourth, fifth, and sixth days after irradiation.

Each aliquot drawn from the three irradiated blood samples was tested for total nucleated blood cells and the number of those cells remaining viable. The number of viable nucleated cells remaining in a sample was determined by treating it with trypan blue which is absorbed by dead nucleated cells and rejected by viable cells.

The date presented in the Table is organized as follows:

Column I—interval after irradiation until evaluation of cell count of the sample (in days).
Column II—nucleated cell count of sample at time of evaluation ($\times 10^4$).
Column III—total nucleated cell count (viable+dead)/nucleated cell count at time zero (percent).
Column IV—viable nucleated cell count/total nucleated cell count at time zero (percent).

| TREATMENT OF 500 cc BLOOD SYSTEM | | | | |
|---|---|---|---|---|
| | I | II | III | IV |
| Control (Not-Irradiated) | 6 | 94 | 94 | 86 |
| Sample Taken After 1 Hour of UVA Exposure | 0 | 71 | 100 | 95 |
| | 3 | 33 | 46 | 35 |
| | 4 | 35 | 49 | 28 |
| | 5 | 21 | 29 | 14 |
| | 6 | 27 | 37 | 13 |
| Sample Taken After 2 Hours of UVA Exposure | 0 | 125 | 100 | 100 |
| | 3 | 83 | 66 | 48 |
| | 4 | 47 | 37 | 21 |
| | 5 | 41 | 32 | 13 |
| | 6 | 13 | 10 | 2 |
| Sample Taken After 3 Hours of UVA Exposure | 0 | 137 | 100 | 97 |
| | 3 | 70 | 51 | 29 |
| | 4 | 43 | 31 | 12 |
| | 5 | 12 | 16 | 2 |
| | 6 | 9 | 7 | 1 |

From the above Table, it is apparent that the invention has produced a rapid destruction of the excess lymphocyte population in the treated blood, without observable clinically adverse effects on other blood constituents. By way of analysis, within six days after treatment according to the subject method the population of viable lymphocyte cells in each blood sample was appreciably reduced. More particularly, within six days after exposure in the described apparatus for periods of 1, 2 and 3 hours, the percentages of viable lymphocytes remaining in the treated blood were respectively reduced to 13, 2 and 1 percent of their original values. By way of comparison, a control sample which was not exposed to UVA had 86 percent of its lymphocyte population viable after the same amount of time.

While the present invention has been particularly described in terms of specific embodiments thereof, it will be understood in view of the present disclosure that numerous variations upon the invention are now enabled to those skilled in the art, which variations yet reside within the scope of the present invention. Accordingly, the invention is to be broadly construed, and limited only by the scope and spirit of the claims now appended hereto.

What is claimed is:

1. A method for reducing the functioning population of a blood constituent in the blood supply of a human subject, comprising the steps of:

withdrawing blood from said subject, and irradiating said withdrawn blood with UV radiation in the presence of an effective amount of a dissolved photoactive chemical agent specific for a receptor site in or on the blood constituent and capable when activated by said UV radiation of forming photo-adducts with blood constituent receptor sites, to thereby effect chemical bonding between said photoactivated chemical agent and said receptor sites, thereby initiating the destruction and/or removal of said blood constituent from the blood supply of the subject and returning the irradiated blood to said subject.

2. The method according to claim 1 wherein the blood constituent comprises activated T-lymphocytes.

3. The method according to claim 1 wherein the photoactivated chemical agent comprises a polypeptide selected from the group consisting of insulin, interleukin, thymopoietin and transferrin, and wherein said agent further comprises a photocytotoxic chemical agent covalently-linked to said polypeptide.

4. The method according to claim 1 wherein the photoactivated chemical agent comprises a liposome, said liposome having an antibody or a polypeptide capable of binding to said constituent receptor site covalently linked to its outer surface, and said liposome internally incorporating an effective amount of a photocytotoxic agent therein.

5. The method according to claim 4 wherein the polypeptide is selected from the group consisting of insulin, interleukin, thymopoietin and transferrin.

6. The method according to claim 4 wherein said antibody is a monoclonal antibody and said liposome is from about 500 angstroms to about 0.5 micrometers in diameter.

7. The method according to claims 3 or 4 wherein the photocytotoxic chemical agent comprises a moiety selected from the group consisting of psoralen, pyrene cholesteryloleate, acridine, porphyrin, fluorescein, rhodamine, 16-diazocortisone, ethidium, transition metal complexes of bleomycin, transition metal complexes of deglycobleomycin and organoplatinum complexes.

8. The method according to claims 3 or 4 wherein the covalent linkage comprises a disulfide moiety.

9. The method according to claim 4 further comprising the step of separating at least portions of said photoactivated chemical agent-blood constituent complex by dialysis, before returning said blood to said subject.

* * * * *